United States Patent
Stanier

(12) 
(10) Patent No.: US 6,399,111 B1
(45) Date of Patent: *Jun. 4, 2002

(54) AMORPHOUS SILICAS AND ORAL COMPOSITIONS

(75) Inventor: Peter W. Stanier, Sandbach (GB)

(73) Assignee: Crosfield Limited, Warrington (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/395,769

(22) Filed: Sep. 14, 1999

Related U.S. Application Data

(63) Continuation of application No. 08/786,036, filed on Jan. 21, 1997, now abandoned.

(30) Foreign Application Priority Data

Jan. 19, 1996 (GB) .............................................. 9601084

(51) Int. Cl.[7] .......................... A61K 33/00; C01B 33/12; C01B 33/18; C01B 33/187; C01B 33/193
(52) U.S. Cl. .......................... 424/724; 424/49; 423/335; 423/339

(58) Field of Search .......................... 423/335, 336–340; 424/49, 724

(56) References Cited

U.S. PATENT DOCUMENTS

| | | | | |
|---|---|---|---|---|
| 5,225,177 A | | 7/1993 | Wason et al. | 423/339 |
| 5,676,932 A | | 10/1997 | Wason et al. | 424/49 |
| 5,964,937 A | * | 10/1999 | Stanier | 106/492 |

FOREIGN PATENT DOCUMENTS

| | | |
|---|---|---|
| EP | 227334 | 7/1987 |
| EP | 0 535 943 A1 | 4/1993 |
| GB | 2 146 317 A | 9/1984 |
| WO | WO 92/02454 | 2/1992 |
| WO | WO 94/10087 | 5/1994 |

* cited by examiner

*Primary Examiner*—John Pak
(74) *Attorney, Agent, or Firm*—Pillsbury Winthrop LLP

(57) ABSTRACT

An amorphous silica having an RDA value of between 40 and 70, an oil absorption capacity of between 90 and 145 cc/100 g and a moisture loss of less than 7% w/w, can be incorporated at a 10% to 25% loading into a transparent toothpaste having a refractive index of below 1.445, this toothpaste having an RDA value of less than 60.

10 Claims, 1 Drawing Sheet

Figure 1.

```
-12  ƎƧE ■
-11  ƧSƷ
-10  ƧƷE
 -9  ƷEB
 -8  EƧS
 -7  SƧƷ
 -6  ƧES
```

```
        ⋮
     ⁸SƷƧ
     ⁷ƧSƷ
     ⁶EƧƷ
     ⁵SBES
     ⁴EƧB
     ³SBƧ
     ²EƧS
     ¹ƧƷS
     ⁰EƧS
    -1 ESƧ
    -2 SƧƷ
    -3 EBS
    -4 ƷSE
    -5 BƷƧ
```

AMORPHOUS SILICAS AND ORAL COMPOSITIONS

This is a continuation of application Ser. No. 08/786,036, filed Jan. 21, 1997 now abandoned.

FIELD OF THE INVENTION

The present invention relates to amorphous silicas particularly used as abrasives in oral compositions. More particularly, the present invention relates to amorphous precipitated silicas with good cleaning properties associated with low abrasion characteristics which are suitable for oral compositions with low refractive index. The present invention further relates to oral compositions containing such silicas.

BACKGROUND OF THE INVENTION

Toothpaste compositions are well characterised in the literature and many compositions are disclosed in patent specifications and other literature. Toothpaste compositions contain a number of specific components for example abrasive agents, fluoride sources, binders, preservatives, humectants, anti plaque agents, colouring agents, water, flavour and other optional ingredients.

Of these components the abrasive agent is required to provide the appropriate cleaning and plaque removal without subjecting the tooth itself to excessive abrasion. Typically a toothpaste composition will contain from about 5% to about 50% preferably up to about 30% by weight of abrasive. Commonly used abrasives are aluminas, calcium carbonates and calcium phosphate. More recently synthetic silicas have been adopted because of their efficient cleaning, compatibility with other ingredients and their physical properties.

An important property of a silica for use in toothpaste formulations is its oil absorption capacity. For a material with the same particle size, this property relates directly to the thickening effect obtained when adding the silica into a toothpaste formulation; the higher the oil absorption capacity the higher the observed thickening effect. Therefore the higher the oil absorption capacity, the lower the volume of silica which can be incorporated into the toothpaste composition.

Another important property of a silica for use in toothpaste formulations is its ability to provide the appropriate cleaning and plaque removal without subjecting the tooth itself to excessive abrasion i.e. without damaging dentine or enamel. Normally cleaning capability is correlated with abrasion properties.

Another important property of a silica for use in transparent toothpaste formulations is its apparent refractive index. Any transparent toothpaste can be characterised by its refractive index. When incorporating an abrasive material into a transparent toothpaste it is important that this abrasive material remains invisible, i.e. that the clarity of the toothpaste remains the same. This is only achieved if the abrasive material has an apparent refractive index which matches the refractive index of the toothpaste. Now, toothpastes can have refractive indices ranging from 1.430 to 1.470. A refractive index of below 1.445 is generally considered as a low refractive index.

There is a market need for toothpastes in the form of clear gels which are absolutely water white. The method for assessing clarity in this invention involves use of a on a white background. This is the RIT Alphanumeric Resolution Test Object, RT 4-74, produced by Graphic Arts Research Center, Rochester Institute of Technology. The ability to discern the symbols clearly through a sample of product of standard thickness (1 cm) is measured. The symbols are numbered from −12 to +13. The higher, more positive the number, the greater the clarity. In the present invention a number of 0 or above is considered to be characteristic of a visually clear toothpaste.

In U.S. Pat. No. 5,225,177 is claimed an amorphous silica having a moisture of 10%, a 5% pH of 7, an oil absorption of less than 125 cc/100 g, a refractive index of 1.45. It is further stated that the precipitated silicas according to this document have an RDA value of at least 40, preferably 70 to 120. A detailed description of the method used for measuring the RDA value is provided and under 'E. Test Run' it is clear that the RDA value which is given is not the RDA of the silica but the RDA of a toothpaste containing this silica. Moreover on column 11 under 'Calculations' it is made clear that the RDA values are given 'for a particular paste'. Now, It is not disclosed what is the nature of the toothpaste and, more importantly, the toothpaste silica loading is not disclosed (6% to 35% according to column 5 line 25). The RDA values therefore refer to the abrasion property of an unknown toothpaste containing an unknown amount of a specific amorphous silica and it is not possible, relying on U.S. Pat. No. 5,225,177 to know what is the RDA value of the silica.

Now, the applicant of U.S. Pat. No. 5,225,177 is marketing a product called Zeodent 115 (Average particle size 9.3 μm, refractive index 1.45, oil absorption 100 cc/100 g) which is believed to be the silica disclosed in U.S. Pat. No. 5,225,177. The RDA value of this silica is 97 which is regarded as a low to medium abrasive silica.

Commercially available silicas can be broadly categorised as low abrasion if less than 90 RDA and medium abrasion if between 110–150 RDA. Samples of commercially available toothpaste silicas were submitted to Missouri Analytical Laboratories and the RDA value of the silica was determined with the following results:

| SILICA NAME | RDA |
| --- | --- |
| ZEODENT 113 | 84 |
| ZEODENT 115 | 97 |
| TIXOSIL 73 | 83 |
| SIDENT 9 | 113 |
| SIDENT 12 | 91 |
| SORBOSIL AC77 | 125 |
| SORBOSIL AC35 | 110 |

(NB: Zeodent, Tixosil, Sident and Sorbosil are registered trade marks of Huber, Rhone Poulenc, Degussa and Crosfield respectively.)

From the data, it can be seen that even current low abrasion silicas have relatively high RDA values and there is a need for an amorphous silica having a much lower RDA value which, when incorporated into an oral composition, exhibits good cleaning characteristics. There is also a need for such an amorphous silica which does not alter the clarity of the toothpaste composition to which it is added.

Now, when referring to oral compositions with good clarity, the trend in the industry is towards formulations with low refractive indices, in order to improve costs. This is because the refractive index of a toothpaste is mainly governed by its humectant/water ratio, with higher ratios giving higher refractive indices. The humectant, for example Sorbitol, is an expensive component with a high refractive index (>1.46), whereas water has a lower refractive index and is cheap.

There is therefore a need for more cost effective oral compositions, which are transparent at a refractive index lower than 1.445, in order to minimise the amount of humectant.

Tests and Definitions i) Oil Absorption

The oil absorption is determined by the ASTM spatula rub-out method (American Society Of Test Material Standards D, 281).

The test is based on the principle of mixing linseed oil with the silica by rubbing with a spatula on a smooth surface until a stiff putty-like paste is formed which will not break or separate when it is cut with a spatula. The volume of oil used is then put into the following equation:

$$\text{Oil absorption} = \frac{\text{cm}^3 \text{ oil absorption} \times 100}{\text{Wt. of silica sample in g}}$$

$$= \text{cm}^3 \text{ oil}/100 \text{ g silica}$$

ii) Weight Mean Particle Size

The weight mean particle size of the silica is determined using a Malvern Mastersizer model X, with a 45 mm lens and MS15 sample presentation unit. This instrument, made by Malvern Instruments, Malvern, Worcestershire uses the principle of Fraunhoffer diffraction, utilising a low power He/Ne laser. Before measurement the sample is dispersed ultrasonically in water for 7 minutes to form an aqueous suspension.

The Malvern Mastersizer measures the weight particle size distribution of the silica. The weight mean particle size ($d_{50}$) or 50 percentile, the 10 percentile ($d_{10}$) and the 90 percentile ($d_{90}$) are easily obtained from the data generated by the instrument.

iii) Loose Bulk Density

Loose bulk density is determined by weighing approximately 180 ml of silica into a dry 250 ml measuring cylinder, inverting the cylinder ten times to remove air pockets and reading the final settled volume.

$$\text{Loose bulk density} = \frac{\text{Weight}}{\text{Volume}} \times 1000 \text{ g/l}$$

iv) Electrolyte Levels

Sulphate is determined gravimetrically by hot water extraction of the silica, followed by precipitation as barium sulphate. Chloride is determined by hot water extraction of the silica, followed by titration with standard silver nitrate solution using potassium chromate as indicator (Mohr's method).

v) Moisture Loss at 105° C.

Moisture loss is determined by the loss in weight of a silica when dried to constant weight in an electric oven at 105° C.

vi) Ignition Loss at 1000° C.

Ignition loss is determined by the loss in weight of a silica when ignited in a furnace at 1000° C. to constant weight.

vii) Structural Water Content

Structural water content is defined by the difference between the ignition loss at 1000° C. and the moisture loss at 105° C.

viii) pH

This measurement is carried out on a 5% w/w suspension of the silica in boiled demineralised water ($CO_2$ free).

ix) BET Surface Area

Surface area is determined using standard nitrogen adsorption methods of Brunauer, Emmett and Teller (BET), using a single point method with a Sorpty 1750 apparatus supplied by Carlo Erba company of Italy. The sample was outgassed under vacuum at 270° C. for 1 hour before measurement.

x) Radioactive Dentine Abrasion Test (RDA)

The procedure follows the method for assessment of dentifrice abrasivity recommended by the American Dental Association (Journal of Dental Research 55 (4) 563, 1976). In this procedure extracted human teeth are irradiated with a neutron flux and subjected to a standard brushing regime. The radioactive phosphorous 32 removed from the dentin in the roots is used as the index of the abrasion of the dentifrice tested. A reference slurry containing 10 g of calcium pyrophosphate in 50 ml of 0.5% aqueous solution of sodium carboxymethyl cellulose is also measured and the RDA of this mixture is arbitrarily taken as 100. The precipitated silica to be tested is prepared as a suspension of 6.25 g in 50 ml of 0.5% aqueous solution of sodium carboxymethyl cellulose and submitted to the same brushing regime.

When testing pastes, 25 g of paste dentifrice are added to 50 ml of water.

xi) Refractive Index (RI)/transmission

The sample of silica is dispersed in a range of Sorbitol syrup (70% Sorbitol)/water mixtures. After de-aeration, usually 1 hour, the transmission of the dispersions is determined using a spectrophotometer at 589 nm; water being used as blank. The refractive index of each dispersion is also measured using an Abbe refractometer.

A graphical representation of transmission plotted against refractive index allows the range of refractive indices over which the transmission exceeds 70% to be determined. The maximum transmission of the sample and the apparent refractive index of silica at which this is obtained can also be estimated from this graph.

General Description of the Invention

It is a first object of the present invention to provide an amorphous silica characterized by:

an RDA value of between 40 and 70, preferably between 50 and 60, a light transmission of more than 70% at a refractive index of below 1.445, preferably between 1.430 and 1.444, most preferably between 1.436 and 1.444.

an oil absorption capacity of between 90 and 145 cm$^3$/100 g, preferably between 100 and 125 cm$^3$/100 g.

Preferably, the amorphous silica of the invention presents a peak of light transmission in the refractive index range of 1.430 to 1.444, most preferably between 1.436 to 1.444. This enables the silica to be incorporated into transparent oral compositions of low refractive indices.

The amorphous silica of the invention presents a structural water content of between 3.5% and 5.0%, preferably between 4.0 and 4.5%, a BET surface area of 50 to 350 m$^2$/g, preferably between 50 and 250 m$^2$/g, a pH in a 5% solution of between 6 and 7.5, a loose bulk density of between 180 and 300 g/l.

It is a second object of the present invention to provide an oral composition comprising an amorphous silica, said amorphous silica having:

an RDA value of between 40 and 70, preferably between 50 and 60, a light transmission of more than 70% at a refractive index of below 1.445.

Preferably, the amorphous silica is a precipitated silica having an oil absorption capacity of between 90 and 145 cm$^3$/100 g, preferably between 100 and 125 cm$^3$/100 g.

It is third object of the present invention to provide a visually clear oral composition having a refractive index of below 1.445, preferably between 1.430 to 1.444, most preferably between 1.436 to 1.444, comprising 5 to 25% by weight, preferably 10 to 25% by weight, of an amorphous silica, said toothpaste composition having an RDA less than 60, preferably less than 50, preferably above 35.

Preferably, the amorphous silica is the amorphous silica of the present invention.

This toothpaste composition is capable of cleaning and polishing human teeth without damaging said teeth.

In the oral compositions according to the present invention, the level of the amorphous silica may be wide ranging, for example depending upon the physical form of the desired end product.

Particularly preferred oral compositions of the invention are in the form of pastes, gels, creams or liquids, the exact physical properties of which may be controlled for example by suitable adjustment of the solid to liquid ratio and/or the viscosity of the liquid phase, e.g. by selecting appropriate contents of adjunct components, as described further below.

In preferred embodiments of the invention, the amorphous silica of the invention is present in the composition in an amount of from about 1 to about 99% by weight, more preferably from about 2 to about 60%, even more preferably from about 3 to about 40%. In liquid or paste compositions of the invention, the amorphous silica of the invention is preferably present in an amount of from about 1 to about 30% by weight, more preferably from about 5 to about 25%.

The oral compositions of the invention may contain one or more additional components, as will now be described.

Oral compositions of the invention preferably comprise one or more surfactants, preferably selected from anionic, nonionic, amphoteric and zwitterionic surfactants, and mixtures thereof, all being suitable for dental and/or oral use.

Suitable anionic surfactants may include soaps, alkyl sulphates, alkyl ether sulphates, alkaryl sulphonates, alkanoyl isethionates, alkanoyl taurates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Example of preferred anionic surfactants may include sodium lauryl sulphate, sodium dodecylbenzene sulphonate, sodium lauroyl sarcosinate and sodium coconut monoglyceride sulphonate.

Nonionic surfactants which may be suitable for use in composition of the invention include sorbitan and polyglycerol esters of fatty acids, as well as ethylene oxide/propylene oxide block copolymers.

Amphoteric surfactants which may be suitable for use in compositions of the invention include betaines such as cocamidopropyl betaine, and sulphobetaines, for example.

The surfactant(s) may be present in the oral composition of the invention in a total amount of from about 0.1 to about 3% by weight.

Water is another preferred component of the oral compositions of the invention and may be present in an amount of from about 1 to about 90% by weight, preferably from about 10 to about 60%, more preferably from about 15 to about 50% and most preferably for clear pastes from about 1 to about 20%.

Toothpastes and creams of this invention may also contain humectants, for example polyols such as glycerol, sorbitol syrup, polyethylene glycol, lactitol, xylitol and hydrogenated corn syrup. The total amount of humectant, if present, may be for example in the range of from about 10 to about 85% by weight of the composition.

In the oral compositions of the present invention it is particularly preferred that one or more thickening agents and/or suspending agents are included, in order to give the composition the desired physical properties (e.g. whether a paste, cream or a liquid) and in order that the amorphous silica of the invention remain stably dispersed throughout the composition.

A particularly preferred means for thickening the oral compositions of the invention is by the inclusion of conventional thickening materials such as thickening silicas, examples of which have already been mentioned above.

Other suitable suspending/thickening agents are well known in the art and include for example polyacrylic acid, copolymers and cross-linked polymers of acrylic acid, copolymers of acrylic acid with a hydrophobic monomer, copolymers of carboxylic acid-containing monomers and acrylic esters, cross-linked copolymers of acrylic acid and acrylate esters, esters of ethylene glycol or esters of polyethylene glycol (e.g. fatty acid esters thereof), heteropolysaccharide gums such as xanthan and guar gums, and cellulose derivatives such as sodium carboxymethyl cellulose.

Particularly suitable thickening agents are xanthan gum and sodium carboxymethyl cellulose.

The thickening agent and/or suspending agent (which may be used singly or as mixtures of two or more such materials) may be present in the composition in a total amount of from about 0.1 to about 50% by weight; preferably from about 0 to about 15%, most preferably from about 1 to about 10% for silica thickening agents; preferably from about 0.1to about 5% for polymer suspending agents.

The compositions of the invention may contain one or more other components conventionally found in oral compositions. Suitable additional ingredients include: flavouring substances, e.g. peppermint, spearmint; artificial sweeteners; perfume or breath freshening substances; pearlescing agents; peroxy compounds, e.g. hydrogen peroxide or peracetic acid; opacifiers; pigments and colourings; preservatives; moisturising agents; fluoride-containing compounds; anti-caries agents; anti-plaque agents; therapeutic agents such as zinc citrate, Triclosan (ex Ciba Geigy); proteins; salts; pH adjusting agents.

Compositions in accordance with the present invention may be made by conventional methods of preparing oral compositions. Pastes and creams may be prepared by conventional techniques, for example using high shear mixing systems under vacuum.

SPECIFIC DESCRIPTION OF THE INVENTION

The invention will be further described in the following examples with reference to FIG. 1 which represents the RIT Alphanumeric Resolution Test Object, RT 4-74, produced by Graphic Arts Research Center, Rochester Institute of Technology.

Example 1

A heated stirred reacton vessel was used for the silicate/acid reaction.

Mixing is an important feature in the reaction of silicate and sulphuric acid. Consequently fixed specifications, as listed in Chemineer Inc. Chem Eng. Apr. 26, 1976 pages 102–110, have been used to design the baffled, heated stirred reaction vessel. Whilst the turbine design is optional to the mixing geometry, a 6-bladed 30° pitched bladed unit has been chosen for the experiments in order to ensure maximum mixing effectiveness with minimum shear.

The solutions used in the process were as follows:

a) Sodium silicate solutions with a $SiO_2:Na_2O$ molar ratio in the range of 2.2 to 2.7:1 and a solids content in the range of 9.0 to 21.5% by weight.

b) A sulphuric acid solution of specific gravity 1.07 (11% w/w solution) to 1.14 (20% w/w solution).

The following procedure was adopted in the preparation of the precipitated silicas. Values of reactant concentrations, volumes, temperatures and ageing steps are given in Table 1.

(A) litres of water were placed in the vessel with (C) litres of sodium silicate solution and (B) grammes of electrolyte. This mixture was then stirred and heated to (H)° C.

(D) litres of sodium silicate and (F) litres of sulphuric acid were then simultaneously added over (G) minutes at (H)° C. The flow rates of the silicate and acid solutions were uniform throughout the addition period to ensure that a constant pH, in the range from 9.0 to 11.5 was maintained in the vessel.

Sulphuric acid solution was then added over a period of (J) minutes to the final end of batch pH (K).

The final slurry was then filtered and washed with water to remove excess electrolyte. Typically, for a toothpaste application, the residual electrolyte would be less than 2% on a dry weight basis. After washing, the filter cake in each example was flash dried to remove the water rapidly from the silica so that the structure is maintained, and comminuted to the desired particle size range.

The precipitated silicas obtained had the properties expressed on a dry weight basis listed in Table 2.

TABLE 1

| TEST | EXAMPLE 1 |
|---|---|
| Vessel Capacity (liters) | 64 |
| Water Volume (A) (liters) | 11.9 |
| Electrolyte (B) (grammes) | 300 |
| Electrolyte type | $Na_2SO_4$ |
| Silicate ratio $SiO_2/Na_2O$ by wt. | 2.26 |
| $SiO_2$ Concn. in Silicate (% w/w) | 14.24 |
| Silicate vol. (C) (liters) | 0.19 |
| Silicate vol. (D) (liters) | 18.5 |
| Acid concn. (% w/w) | 17.6 |
| Acid I vol. (F) (liters) | 9.4 |
| Sol Time (G) (mins.) | 40 |
| Temperature (H) (° C.) | 88 |
| Acid II addition time (J) (mins.) | 9.5 |
| End of batch pH (K) | 3.5 |

TABLE 2

| TEST | EXAMPLE 1 |
|---|---|
| Silica RDA | 49 |
| Max. % Transmission | 98 |
| At Refractive Index of | 1.442 |
| Oil Absorption (mls/100 g) | 120 |
| pH | 6.2 |
| A.p.s. (um) | 7.3 |
| Moisture loss @ 105° C. | 4.5 |
| Ignition Loss @ 1000° C. | 8.5 |
| SA (m2/g) | 75 |

TABLE 2-continued

| TEST | EXAMPLE 1 |
|---|---|
| SO4= (%) | 0.1 |
| Cl- (%) | 0.01 |
| Loose Bulk Density (g/l) | 285 |

Examples 2 and 3

The amorphous silica prepared as described in example 1 was formulated at 8 and 10% loading to produce transparent toothpastes formulations.

The general formulations were as follows:

| Ingredient | Example 2 (% w/w) | Example 3 (% w/w) |
|---|---|---|
| Sorbitol | 58.0 | 58.0 |
| Water | 14.99 | 13.74 |
| Silica of the Invention (Example 1) | 8.0 | 10.0 |
| Sorbosil TC15 (*) | 9.5 | 8.75 |
| Other active ingredients | to 100% | to 100% |
| Refractive index | 1.4386 | 1.4425 |
| Clarity number | +3 | +13 |

The RDA values of these toothpastes were less than 60.
(*) Sorbosil TC15 is thickening silica produced by Crosfield ltd.

These formulations produced visually clear pastes, especially example 3, which had exceptional clarity.

What is claimed is:

1. Amorphous silica having:
   an RDA value of between 40 and 70;
   a light transmission of more than 70% at a refractive index of below 1.445;
   an oil absorption capacity of between 90 and 145 $cm^3$/100 g;
   a structural water content of between 3.5% and 5.0%, and
   a BET surface area of between 50 and 250 $m^2$/g.

2. Amorphous silica according to claim 1 wherein said refractive index is between 1.430 to 1.444.

3. The amorphous silica according to claim 1 wherein said refractive index is between 1.436 and 1.444.

4. The amorphous silica according to claim 1 wherein said RDA value is between 50 and 60.

5. The amorphous silica according to claim 1 wherein said oil absorption capacity is between 100 and 125 $cm^3$/100 g.

6. Amorphous silica having:
   an RDA value of between 40 and 70;
   a light transmission of more than 70% at a refractive index of below 1.445;
   an oil absorption capacity of between 90 and 145 $cm^3$/100 g;
   a structural water content of between 3.5% and 5.0%, and
   a BET surface area of between 50 and 250 $m^2$/g;
   a pH in a 5% solution of between 6 and 7.5; and
   a loose bulk density of between 180 and 300 g/l.

7. The amorphous silica according to claim 6 wherein said refractive index is between 1.430 to 1.444.

8. The amorphous silica according to claim 6 wherein said refractive index is between 1.436 and 1.444.

9. The amorphous silica according to claim 6 wherein said RDA value is between 50 and 60.

10. The amorphous silica according to claim 1 wherein said oil absorption capacity is between 100 and 125 $cm^3$/100 g.

* * * * *